US012745926B2

(12) United States Patent
Holman et al.

(10) Patent No.: US 12,745,926 B2
(45) Date of Patent: Sep. 29, 2026

(54) CAPACTIVE BASED MECHANOMYOGRAPHY

(71) Applicant: Tactual Labs Co., New York, NY (US)

(72) Inventors: David Holman, Toronto (CA); Valkyrie Savage, Toronto (CA); Kevin Stager, Austin, TX (US); Faizan Haque, Mississauga (CA); Yanjun Jiang, Toronto (CA); Steven Sanders, New York, NY (US)

(73) Assignee: Tactual Labs Co., New York, NY (US)

( * ) Notice: Subject to any disclaimer, the term of this patent is extended or adjusted under 35 U.S.C. 154(b) by 0 days.

(21) Appl. No.: 17/062,608

(22) Filed: Oct. 4, 2020

(65) Prior Publication Data

US 2021/0100482 A1 Apr. 8, 2021

Related U.S. Application Data

(60) Provisional application No. 62/965,425, filed on Jan. 24, 2020, provisional application No. 62/910,528, filed on Oct. 4, 2019.

(51) Int. Cl.

*A61B 5/11* (2006.01)
*G01H 11/08* (2006.01)

(52) U.S. Cl.

CPC .......... *A61B 5/1126* (2013.01); *A61B 5/1107* (2013.01); *A61B 5/1125* (2013.01); *G01H 11/08* (2013.01)

(58) Field of Classification Search

None

See application file for complete search history.

(56) References Cited

U.S. PATENT DOCUMENTS

| | | | | |
|---|---|---|---|---|
| 2015/0091790 | A1 * | 4/2015 | Forutanpour | G06F 3/011 345/156 |
| 2016/0143592 | A1 * | 5/2016 | Martikka | A61B 5/11 600/301 |
| 2017/0136264 | A1 * | 5/2017 | Hyde | G16H 50/30 |
| 2018/0229674 | A1 * | 8/2018 | Heinrich | A61B 5/18 |
| 2018/0267599 | A1 * | 9/2018 | Holman | G06F 3/017 |
| 2019/0227627 | A1 * | 7/2019 | Kaifosh | G06F 3/017 |

* cited by examiner

*Primary Examiner* — Aurelie H Tu

(74) *Attorney, Agent, or Firm* — Tod Kupstas

(57) ABSTRACT

A sensor system for determining activity of muscles. A plurality of receiving antennas are located on a wearable located proximate to a user skin's surface. A transmitting antenna is located at a location proximate to a user's skin. The transmitting antenna transmits infuses a signal to a user. Measurements of the infused signal are performed on the signals received by the receiving antennas. The measurements of the infused signal are processed and activity of the muscles of the user is determined based on the processed measurements.

11 Claims, 9 Drawing Sheets

CAPACTIVE BASED MECHANOMYOGRAPHY

This application claims the benefit of U.S. Provisional Application Ser. No. 62/910,528, filed Oct. 4, 2019 and U.S. Provisional Application Ser. No. 62/965,425, filed Jan. 24, 2020, the contents of both of which are incorporated herein by reference. This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The disclosed systems relate in general to the field of sensing, and in particular to sensors that determine movements related to muscle activity.

BRIEF DESCRIPTION OF THE DRAWINGS

The foregoing and other objects, features, and advantages of the disclosure will be apparent from the following more particular description of embodiments as illustrated in the accompanying drawings in which reference characters refer to the same parts throughout the various views. The drawings are not necessarily to scale, emphasis instead being placed upon illustrating principles of the disclosed embodiments.

DETAILED DESCRIPTION

Figure 1:
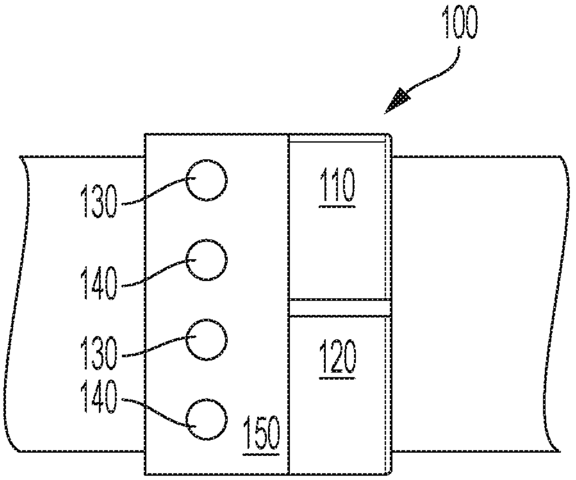
FIG. 1 is a schematic view of a sensor system.

In various embodiments, the present disclosure is directed to sensor systems sensitive to the determination of muscle activity and how it impacts movement within and of the body. In particular, the determination and sensing of the mechanical oscillation and vibration caused by muscles is determined capacitively using the sensing systems set forth herein. The determination and sensing of mechanical oscillation and vibration of muscles is generally referred to as mechanomyography. While the terms "mechanography" and "mechanomyogram" are used herein to refer to, among other things, the activity of muscles it should also be understood that these terms also encompass the signals that are measured and processed that are the result of muscle activity, and which may be impacted by the transmission of signals in and on the body, or by the presence of bones, vessels, ligaments, air cavities, etc. and subsequent movement of the skin's surface. In an embodiment, received signals may be processed to thereby form mechanomyograms which can be correlated to a particular response, e.g., muscle activity. In an embodiment, mechanomyograms can reveal, or be indicative of, oscillation of muscles, vibrations of muscles, or resonance of muscles. In an embodiment, a mechanomyogram can be used to determine gross movement, isometric activity and passive activity and the load on a given muscle.

Throughout this disclosure, the term "event" may be used to describe periods of time in which muscle activity is detected. In accordance with an embodiment, events may be detected, processed, and/or supplied to downstream computational processes with very low latency, e.g., on the order of ten milliseconds or less, or on the order of less than one millisecond.

As used herein, and especially within the claims, ordinal terms such as first and second are not intended, in and of themselves, to imply sequence, time or uniqueness, but rather, are used to distinguish one claimed construct from another. In some uses where the context dictates, these terms may imply that the first and second are unique. For example, where an event occurs at a first time, and another event occurs at a second time, there is no intended implication that the first time occurs before the second time, after the second time or simultaneously with the second time. However, where the further limitation that the second time is after the first time is presented in the claim, the context would require reading the first time and the second time to be unique times. Similarly, where the context so dictates or permits, ordinal terms are intended to be broadly construed so that the two identified claim constructs can be of the same characteristic or of different characteristics. Thus, for example, a first and a second frequency, absent further limitation, could be the same frequency, e.g., the first frequency being 10 Mhz and the second frequency being 10 Mhz; or could be different frequencies, e.g., the first frequency being 10 Mhz and the second frequency being 11 Mhz. Context may dictate otherwise, for example, where a first and a second frequency are further limited to being frequency-orthogonal to each other, in which case, they could not be the same frequency.

The present application contemplates various embodiments of sensors designed for implementation in sensing systems. The sensor configurations described herein are suited for use with frequency-orthogonal signaling techniques (see, e.g., U.S. Pat. Nos. 9,019,224; 9,529,476; and 9,811,214, all of which are hereby incorporated herein by reference). The sensor configurations discussed herein may be used with other signal techniques, including scanning or time division techniques, and/or code division techniques. It is pertinent to note that the sensors described and illustrated herein are also suitable for use in connection with signal infusion (also referred to as signal injection) techniques and apparatuses. Signal infusion being a technique in which signal is transmitted to a person, that signal being capable of travelling on, within and through the person. In an embodiment, an infused signal causes the object of infusion (e.g., a hand, finger, arm or entire person) to become a transmitter of the signal.

The presently disclosed systems and methods further involve principles related to and for designing, manufacturing and using capacitive based sensors and capacitive based sensors that employ a multiplexing scheme based on orthogonal signaling such as but not limited to frequency-division multiplexing (FDM), code-division multiplexing (CDM), or a hybrid modulation technique that combines both FDM and CDM methods. References to frequency herein could also refer to other orthogonal signal bases. As such, this application incorporates by reference Applicants' prior U.S. Pat. No. 9,019,224, entitled "Low-Latency Touch Sensitive Device" and U.S. Pat. No. 9,158,411 entitled "Fast Multi-Touch Post Processing." These applications contemplate FDM, CDM, or FDM/CDM hybrid touch sensors having concepts that are germane to and able to be used in connection with the presently disclosed sensors. In the aforementioned sensors, interactions are sensed when a signal from a row conductor is coupled (increased) or decoupled (decreased) to a column conductor and the result detected from that column conductor. By sequentially exciting the row conductors and measuring the coupling of the excitation signal at the column conductors, a heatmap reflecting capacitance changes of the sensor, and thus proximity to the sensor, can be created.

This application also employs principles used in fast multi-touch sensors and other interfaces disclosed in the following: U.S. Pat. Nos. 9,933,880; 9,019,224; 9,811,214; 9,804,721; 9,710,113; 9,158,411; 10,191,579; 10,386,975; and 10,175,772. Familiarity with the disclosure, concepts and nomenclature within these patents is presumed. The entire disclosure of these patents and applications incorporated therein by reference are incorporated herein by reference. This application also employs principles used in fast multi-touch sensors and other interfaces disclosed in the following: U.S. patent application Ser. Nos. 15/195,675; 15/821,677; 15/904,953; 15/905,465; 15/943,221; 16/102,185; and U.S. Provisional Patent Application Nos. 62/540,458; 62/575,005; 62/621,117; 62/619,656; 62/866,324; and PCT Publication No. PCT/US2017/050547, familiarity with the disclosures, concepts and nomenclature therein is presumed. The entire disclosure of those applications and the applications incorporated therein by reference are incorporated herein by reference.

Certain principles of a fast multi-touch (FMT) sensor have been disclosed in the patent applications discussed above. Orthogonal signals may be transmitted into a plurality of transmitting conductors (or antennas) and information may be received by receivers attached to a plurality of receiving conductors (or antennas). In an embodiment, receivers "sample" the signal present on the receiving conductors (or antennas) during a sampling period ($\tau$). In an embodiment, signal (e.g., the sampled signal) is then analyzed by a signal processor to identify touch events (including, e.g., actual touch, near touch, hover and farther away events that cause a change in coupling between a transmitter and receiver). In an embodiment, one or more transmitting conductors (or antennas) can move with respect to one or more receiving conductors (or antennas), and such movement causes a change of coupling between at least one of the transmitting conductors (or antennas) and at least one of the receiving conductors (or antennas). The transmitting conductors and receiving conductors may be organized in a variety of configurations, including, e.g., a matrix where the crossing points form nodes, and interactions are detected by processing of received signals. In an embodiment where the orthogonal signals are frequency orthogonal, spacing between the orthogonal frequencies, $\Delta f$, is at least the reciprocal of the measurement period $\tau$, the measurement period $\tau$ being equal to the period during which the column conductors are sampled. Thus, in an embodiment, the received at a column conductor may be measured for one millisecond ($\tau$) using frequency spacing ($\Delta f$) of one kilohertz (i.e., $\Delta f=1/\tau$).

In an embodiment, the signal processor of a mixed signal integrated circuit (or a downstream component or software) is adapted to determine at least one value representing each frequency orthogonal signal transmitted to (or present on) a row conductor (or antenna). In an embodiment, the signal processor of the mixed signal integrated circuit (or a downstream component or software) performs a Fourier transform on the signals present on a receive conductor or antenna. In an embodiment, the mixed signal integrated circuit is adapted to digitize received signals. In an embodiment, the mixed signal integrated circuit (or a downstream component or software) is adapted to digitize the signals present on the receive conductor or antenna and perform a discrete Fourier transform (DFT) on the digitized information. In an embodiment, the mixed signal integrated circuit (or a downstream component or software) is adapted to digitize the signals present on the received conductor or antenna and perform a Fast Fourier transform (FFT) on the digitized information—an FFT being one type of discrete Fourier transform.

It will be apparent to a person of skill in the art in view of this disclosure that a DFT, in essence, treats the sequence of digital samples (e.g., window) taken during a sampling period (e.g., integration period) as though it repeats. As a consequence, signals that are not center frequencies (i.e., not integer multiples of the reciprocal of the integration period (which reciprocal defines the minimum frequency spacing)), may have relatively nominal, but unintended consequence of contributing small values into other DFT bins. Thus, it will also be apparent to a person of skill in the art in view of this disclosure that the term orthogonal as used herein is not "violated" by such small contributions. In other words, as the term frequency orthogonal is used herein, two signals are considered frequency orthogonal if substantially all of the contribution of one signal to the DFT bins is made to different DFT bins than substantially all of the contribution of the other signal.

When sampling, in an embodiment, received signals are sampled at at least 1 MHz. In an embodiment, received signals are sampled at at least 2 MHz. In an embodiment, received signals are sampled at 4 Mhz. In an embodiment, received signals are sampled at 4.096 Mhz. In an embodiment, received signals are sampled at more than 4 MHz. To achieve kHz sampling, for example, 4096 samples may be taken at 4.096 MHz. In such an embodiment, the integration period is 1 millisecond, which per the constraint that the frequency spacing should be greater than or equal to the reciprocal of the integration period provides a minimum frequency spacing of 1 KHz. (It will be apparent to one of skill in the art in view of this disclosure that taking 4096 samples at e.g., 4 MHz would yield an integration period slightly longer than a millisecond, and not achieving kHz sampling, and a minimum frequency spacing of 976.5625 Hz.) In an embodiment, the frequency spacing is equal to the reciprocal of the integration period. In such an embodiment, the maximum frequency of a frequency-orthogonal signal range should be less than 2 MHz. In such an embodiment, the practical maximum frequency of a frequency-orthogonal signal range should be less than about 40% of the sampling rate, or about 1.6 MHz. In an embodiment, a DFT (which could be an FFT) is used to transform the digitized received signals into bins of information, each reflecting the frequency of a frequency-orthogonal signal transmitted which may have been transmitted by the transmit antenna 130. In an embodiment 2048 bins correspond to frequencies from 1 KHz to about 2 MHz. It will be apparent to a person of skill in the art in view of this disclosure that these examples are simply that, exemplary. Depending on the needs of a system, and subject to the constraints described above, the sample rate may be increased or decreased, the integration period may be adjusted, the frequency range may be adjusted, etc.

In an embodiment, a DFT (which can be an FFT) output comprises a bin for each frequency-orthogonal signal that is transmitted. In an embodiment, each DFT (which can be an FFT) bin comprises an in-phase (I) and quadrature (Q) component. In an embodiment, the sum of the squares of the I and Q components is used as a measure corresponding to signal strength for that bin. In an embodiment, the square root of the sum of the squares of the I and Q components is used as measure corresponding to signal strength for that bin. It will be apparent to a person of skill in the art in view of this disclosure that a measure corresponding to the signal strength for a bin could be used as a measure related to muscle activity. In other words, the measure corresponding to signal strength in a given bin would change as a result of some activity originated by muscles of the body.

Turning to FIG. 1, a simplified diagram of a sensing system 100 that is incorporated into a wearable 150 is shown. The sensing system 100 is generally able to discern activity that occurs within the vicinity of the wearable 150. In FIG. 1, the wearable 150 is placed on a wrist. In an embodiment, a mixed signal integrated circuit with signal processing capabilities comprises a transmitter 110, and a receiver 120. In an embodiment, an analog front end comprising a transmitter (or multiple transmitters) and a receiver (or multiple receivers) is used to send and receive signals instead of the mixed signal integrated circuit. In such an embodiment, the analog front end provides a digital interface to signal generating and signal processing circuits and/or software. In an embodiment, the mixed signal integrated circuit is adapted to generate one or more signals and send the signals to the transmitting antennas 130 via the transmitter 110. In an embodiment, the mixed signal integrated circuit is adapted to generate a plurality of frequency-orthogonal signals and send the plurality of frequency-orthogonal signals to the transmitting antennas 130.

The transmitter 110 is conductively coupled to transmitting antennas 130, and the receiver 120 is operably connected to receiving antennas 140. The transmitting antennas 130 are supported on the wearable 150 that is worn on a body part. It will be apparent to a person of skill in the art in view of this disclosure that the transmitter and receivers are arbitrarily assigned, and the transmitter 110 and transmitting antenna 130 can be used on the receive side, while the receiver 120, and the receiving antenna 140 can be used as the transmit side. It will also be apparent to a person of skill in the art in view of this disclosure that the signal processor, transmitter and receiver may be implemented on separate circuits. It will be apparent to a person of skill in the art in view of this disclosure that the transmitter and receivers may each support more than one antenna. In an embodiment, a plurality of transmitting antennas 130 and/or a plurality of receiving antennas 140 are employed. With the configuration shown in FIG. 1 it is possible to determine information based on measurements of the signals received. Information regarding activity that occurs in proximity to the transmitting antennas 130 and receiving antennas 140 can be established based on measurements made. These measurements may generally be used to determine movement of fingers and the pose of the hand, however some activities, such as pinch (also referred to as opposition), pinch of two fingers, the touching of an object versus another finger, etc. remain elusive with such the sensor system 100.

In addition to the determination of information regarding what occurs in proximity to the transmitting and receiving antennas or conductors, as described above, it has also been discovered that it is possible to infuse a signal into a person or conductive object and that the infused signal will impact a sensor in proximity to the infused person or object. In U.S. patent application Ser. No. 16/193,476, entitled "System and Methods for Infusion Range Sensor," incorporated herein by reference, a method and system for measuring the distance of an infused object from a sensor was discussed. In that application, a body part or an object was infused with a signal and moved with respect to a sensor. Through the movement of the infused body part or object, the system was able to determine measurements based on the received signals and determine the position of the body part or object from the sensor.

Building off the insights learned from the aforementioned disclosure regarding determining the position of a person or object infused with a signal, further uses of infusion were explored. A person or object that has the signal infused therein can impact a sensor system and what the receivers in the sensor system measure. In an embodiment, an infused signal is frequency orthogonal with respect to the other signals transmitted and received by the sensing apparatus. Generally, as the term is used herein, infusion refers to the process of transmitting signals to the body of a subject, effectively allowing the body (or parts of the body) to become an active transmitting source of the signal. In an embodiment, an electrical signal is injected into the hand (or other part of the body) and this signal can be detected by a sensor even when the hand (or fingers or other part of the body) are not in direct contact with the sensor's touch surface. To some degree, this allows the proximity and orientation of the hand (or finger or some other body part) to be determined, relative to a surface. In an embodiment, signals are carried (e.g., conducted) by the body, and depending on the frequencies involved, may be carried near the surface or below the surface. In an embodiment, frequencies of at least the KHz range may be used in frequency infusion. In an embodiment, frequencies in the MHz range may be used in frequency infusion. To use infusion in connection with FMT as described above, in an embodiment, an infusion signal can be selected to be orthogonal to the transmitted signals, and thus it can be seen in addition to other signals being transmitted.

Further discussion regarding the implementation of the transmitting antennas (or conductors) and receiving antennas (or conductors) in association with wearables can be found in U.S. patent application Ser. No. 15/926,478, U.S. patent application Ser. No. 15/904,953, U.S. patent application Ser. No. 16/383,090 and U.S. patent application Ser. No. 16/383,996, the contents of all of the aforementioned applications incorporated herein by reference.

While the embodiment shown and described in FIG. 1 is able to determine and distinguish movement and position of fingers, it has been discovered that implementations of the transmitting antennas and the receiving antennas can be used to determine information regarding the activity of muscles within the body. In accomplishing this, signals infused into a user can be implemented in a system where the infused signal is received and measurements of the received signal or signals are able to be used in order to determine the activity of muscles. Arrangements of transmitting antennas and receiving antennas are used in order to obtain, among other things, information that is obtained via traditional mechanomyography, as well as information regarding muscle activity and how it correlates to the movement and activity of various parts of the body.

Traditional mechanomyography is accomplished via techniques using a microphone, accelerometer or a piezoresistive sensor. Gross changes in measured signals correspond to muscle contractions. Other detected vibrations reflect the resonant frequency of a muscle. Mechanomyography can be used for accessing muscle fatigue, strength and balance. A mechanomyogram (MMG) is created from the signal generated via mechanical activity and observable from the activity of a muscle when the muscle is contracted or otherwise active. At the onset of muscle contraction, gross changes in the muscle shape cause large peaks in the MMG, while lesser changes cause smaller fluctuations in the signal, i.e. smaller fluctuations. In implementations of the sensing systems discussed herein information reflecting activity of the muscles can be obtained via the measurements of the signal or signals received and processed by the receiving antennas.

Figure 2:
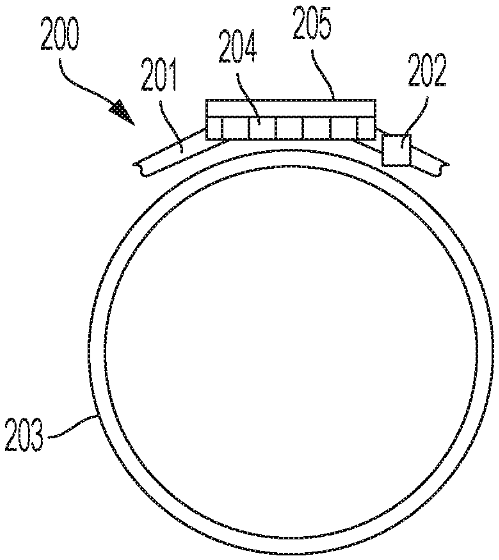
FIG. 2 is a diagram of a sensor system adapted to determine muscle activity.

FIG. 2 is a diagram showing an embodiment of a sensing system 200 located proximate to a wrist area 203. Sensing system 200 is operably attached to a body at a location where information regarding the activity of a particular muscle or muscle grouping is able to be determined. In FIG. 2, sensing system 200 is connected to the wrist area 203 via the use of a band 201. In the arrangement depicted in FIG. 2 the activity of muscles that control motion of the hand are able to be detected. However, it should be understood, and, as discussed below, sensing systems may be operably connected to other parts of the body and/or operably connected to the body using other mechanisms other than bands. The sensing system 200 comprises receiving antennas 204 (antennas are also referred to as conductors or electrodes) that are operably connected to a processor (not shown). The receiving antennas 204 are located within a housing 205. The housing 205 is operably attached to the band 201.

When the sensing system 200 is worn, the receiving antennas 204 are adapted to be located above the surface of the skin of the wrist area 203. In the embodiment, shown in FIG. 2, each of the receiving antennas 204 are located at substantially the same distance from the surface of the wrist area 203 in a direction normal to the surface of the wrist area 203. The receiving antennas 204 may be separated from the surface of the wrist area 203 by material formed from the housing 205. In an embodiment, the band 201 separates the receiving antennas 204 from the surface of the wrist area 203. In an embodiment, a layer of material other than the band separates the receiving antennas from the surface of the skin. In an embodiment, a housing separates the receiving antenna or receiving antennas from the surface of the skin. In an embodiment, multiple layers of material separate the receiving antenna or receiving antennas from the surface of the skin. In an embodiment, a receiving antenna or receiving antennas are placed proximate to the surface of the skin without any intervening layers. In an embodiment, a receiving antenna or receiving antennas are placed on the surface of the skin.

When receiving antennas 204 are located distally from the surface of the skin there is less likelihood of factors such as sweat, skin chemistry, texture, biological factors, etc. from interfering with the measurements. In an embodiment, the receiving antennas 204 are adapted to be positioned about 2 mm from the surface of the skin. In an embodiment, the receiving antennas 204 are adapted to be positioned about 1 mm from the surface of the skin. In an embodiment, the receiving antennas 204 are adapted to be positioned about 3 mm from the surface of the skin. In an embodiment, the receiving antennas 204 are adapted to be positioned about 4 mm from the surface of the skin. In an embodiment, the receiving antennas 204 are adapted to be positioned about 5 mm from the surface of the skin. In an embodiment, some receiving antennas are positioned at different differences from the surface of the skin. For example, one grouping of receiving antennas is positioned at 1 mm from the surface of the skin, while another grouping of receiving antennas is positioned at 2 mm from the surface of the skin. In an embodiment, each of the receiving antennas are positioned at a different distance from the surface of the skin. Generally, as the receiving antennas 204 approach, or are located in proximity to the surface of the skin, the magnitude of the infused signal received from the skin increases. Other factors that impact the reception of infused signal by the receiving antennas are the geometry of the receiving antennas and size of the receiving antennas.

The sensing system 200 also comprises transmitting antenna 202 (also referred to as a conductor or electrode). While a single transmitting antenna 202 is shown more than one transmitting antenna may be used in the sensing system 200. More transmitting antennas can provide additional sources of signal that when measured and processed can provide additional information regarding the activity of muscles. The transmitting antenna 202 is adapted to infuse a signal into the user of the sensing system 200. The transmitting antenna 202 is operably connected to the band 201 and is located sufficiently proximate to the user so as to effectively transmit signal into the user so that the signal is able to be carried by the user. In an embodiment, the band 201 separates the transmitting antenna 202 from the surface of the wrist area 203. In an embodiment, a layer of material other than the band separates a transmitting antenna or transmitting antennas from the surface of the skin. In an embodiment, a housing separates the transmitting antenna or transmitting antennas from the surface of the skin. In an embodiment, multiple layers of material separate a transmitting antenna or transmitting antennas from the surface of the skin. In an embodiment, a transmitting antenna or transmitting antennas are placed proximate to the surface of the skin without any intervening layers. In an embodiment, a transmitting antenna or transmitting antennas are placed on the surface of the skin. The distance of the transmitting antenna from the surface of the skin or whether the transmitting antenna is located on the skin may be determined by factors such as signal strength and body chemistry.

In FIG. 2, the transmitting antenna 202 is shown located distally from the receiving antennas 204, however it should be understood that the transmitting antenna 202 may be located at various distances from the respective receiving antennas 202. The proximity of the transmitting antenna 202 to a receiving antenna 204 may impact the measurements of the signal received by the receiving antennas 204. It should also be understood that the roles of the transmitting antenna and the receiving antennas may switch or alternate in some embodiments, with the transmitting antenna functioning as receiving antenna and the receiving antennas functioning as transmitting antennas.

In FIG. 2, a transmitting antenna 202 is shown that infuses a signal to a user of the sensing system 200. In an embodiment, more than one transmitting antenna infuses a signal to a user. In an embodiment, more than one transmitting antenna infuses a signal to a user wherein each of the transmitting antennas infuses a signal that is orthogonal from each other signal transmitted to the user. In an embodiment, one transmitting antenna infuses more than one signal to a user wherein each of the signals transmitted to the user is orthogonal with respect to each other signal transmitted to the user. By using more transmitted signals potentially more information regarding the location being measured can be obtained.

While the transmitting antenna 202 is shown located on the band 203, it should be understood that the transmitting antenna 202 does not have to be located on the band 203 or necessarily proximate to the band 201. In an embodiment the transmitting antenna or antennas are located on a wearable located elsewhere on the body. In an embodiment, the transmitting antenna or antennas are located proximate to another hand of the user. In an embodiment the transmitting antenna or antennas are located on a ring worn by the user. In an embodiment the transmitting antenna or antennas are located on goggles or glasses located on the head. In an embodiment the transmitting antenna or antennas are located in an article of clothing worn by the user. In an embodiment the transmitting antenna or antennas are located on a token carried by the user.

In an embodiment, the transmitting antenna or antennas are located within the environment and signal is transmitted to the user upon being proximate to the transmitting antenna. In an embodiment, the transmitting antenna or antennas are located in a chair in which the user sits. In an embodiment, the transmitting antenna or antennas are located on the floor on which the user stands. In an embodiment, the transmitting antenna or antennas are located within a vehicle.

In FIG. 2 the geometry is set forth so that there is one transmitting antenna 202 and a plurality of receiving antennas 204. In an embodiment, the roles of the transmitting antenna and receiving antennas may be reversed or alternated. In an embodiment, a receiving antenna or receiving antennas are switched to perform the role of a transmitting antenna or transmitting antennas and the transmitting antenna or transmitting antennas are switched to perform the role of a receiving antenna or receiving antennas. By alternating roles of the antennas additional and different information may be obtained.

Figure 3:
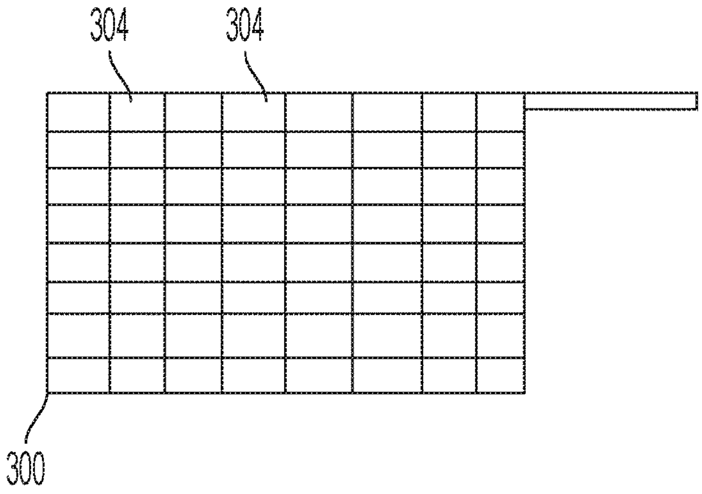
FIG. 3 is a diagram of a receiving antenna array implemented in the sensor system shown in FIG. 2.

Turning to FIG. 3, shown is an antenna array 300 that is formed using a plurality of receiving antennas 304. In an embodiment, the antenna array 300 is used in the sensor system 200 shown in FIG. 2 to provide the receiving antennas. As shown, the antenna array 300 has a plurality of receiving antennas 304. The receiving antennas 304 shown in FIG. 3 are square shaped. In an embodiment, rectangular shaped receiving antennas are used to form the antenna array. In an embodiment, triangular shaped receiving antennas are used to form the antenna array. In an embodiment hexagonal shaped receiving antennas are used to form the antenna array. In an embodiment, more than one type of polygon is used provided that the polygons can form a tessellation or mosaic planar structure that forms the antenna array. In an embodiment, the antenna array is formed using non-polygonal shapes to form the antenna array. In an embodiment, the antenna array is formed using circular antennas. The more simple the geometry used the easier the measurement and computation of signals. In an embodiment, the antenna array is formed from a plurality of antennas that are shaped so as to be able to conform the antenna array to a physiological structure of a person. In an embodiment, the antenna array is formed from a plurality of antennas that are shaped so as to be able to conform the antenna array to a physiological structure of an animal. In an embodiment, the antenna array is formed from a plurality of antennas that are shaped so as to be able to conform the antenna array to a physical structure of an object.

Figure 4:
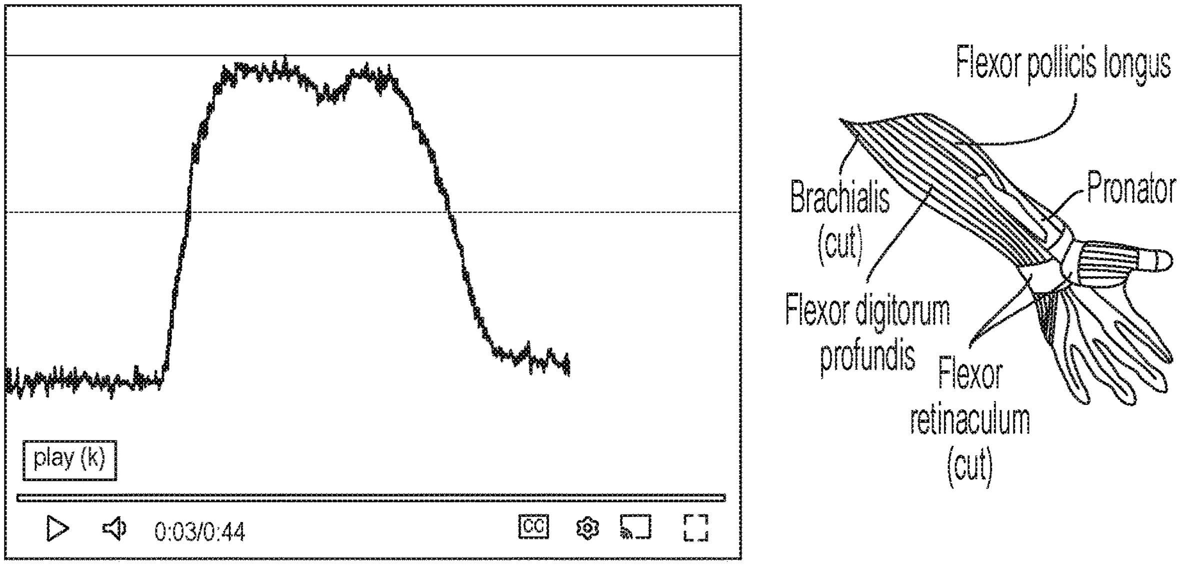
FIG. 4 is an example mechanomyogram showing when a pinch occurred.

The receiving antennas 304 shown in FIG. 4 have a surface area of 25 $mm^2$. Generally, the surface area of each antenna is within the range of 0.005 $mm^2$ to 100 $mm^2$. Preferably the surface area of each antenna is within the range of 0.1 $mm^2$ to 50 $mm^2$. In an embodiment, the receiving antennas have a surface area of 16 $mm^2$. In an embodiment, the receiving antennas have a surface area of 9 $mm^2$. In an embodiment, the receiving antennas have a surface area of 4 $mm^2$. In an embodiment, the receiving antennas have a surface area of 36 $mm^2$. In an embodiment, the receiving antennas are formed from an array of receiving antennas wherein the receiving antennas have different surface areas, In an embodiment, the receiving antennas have surface areas that are two different sized surface areas, for example a 25 $mm^2$ and 4 $mm^2$. Preferably the size, shape, patterning and positioning of the receiving antennas and or transmitting antennas is such that the measurements obtained are commensurate with the goal. Depending on where on the body of a person, object or animal, that the sensor system is to be located and/or what is to be detected can in part determine the particular geometry and positioning of the sensor system that is to be implemented.

Figure 5:
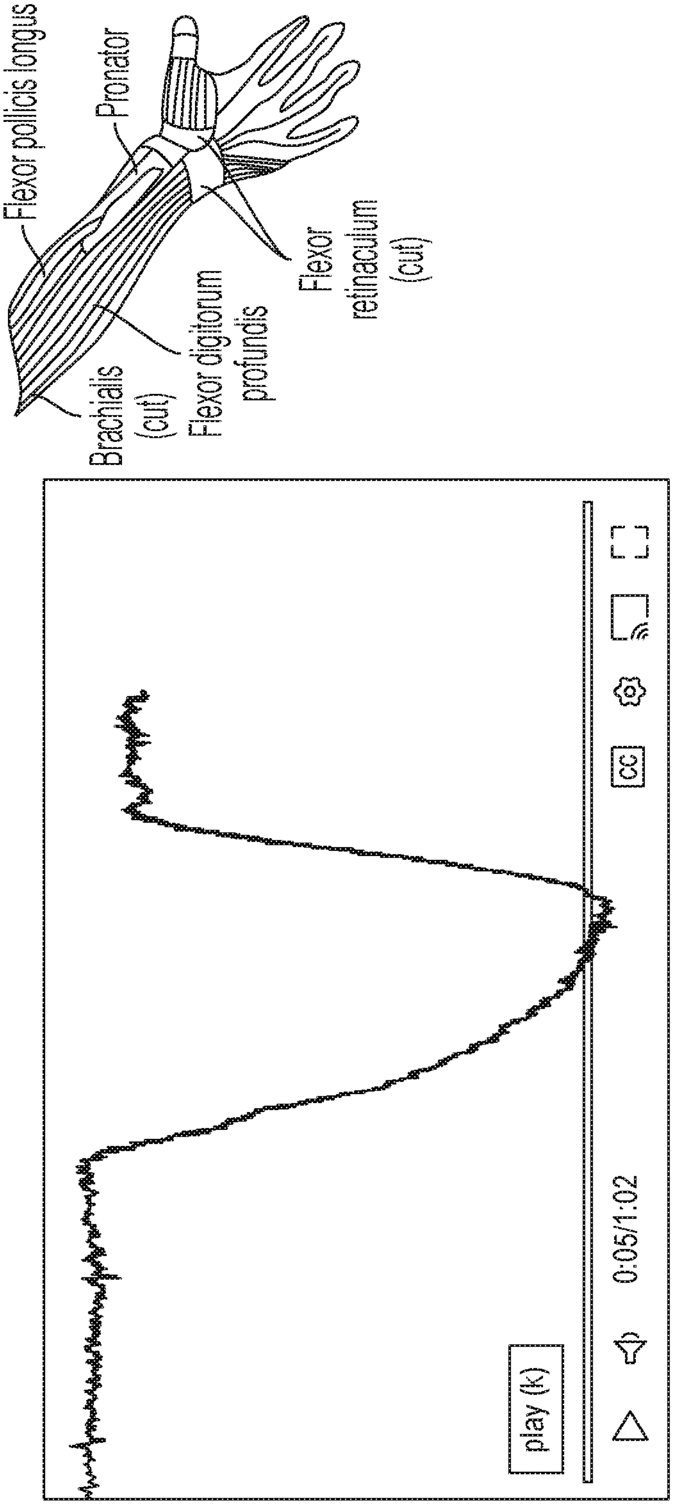
FIG. 5 is another example of a mechanomyogram showing release of a pinch.

Referring now to FIGS. 4 and 5, implementation of a sensor system discussed above is described with respect to determining the activity of muscles. In operation of the sensor system, a transmitting antenna transmits (i.e. infuses) a signal or signals to a user. The anatomy of a user and the movement of muscles impacts the movement of the skin's surface and the behavior of signals that have been infused into a user. The movement of the skin's surface impacts the measurements of the signal that is transmitted into the user and received by the receiving antennas. These measurements are processed and used to determine activity related to the muscles of a user. The activity can be correlated with specific movements of a person or used to determine information regarding a user. In an embodiment, a measurement of a signal transmitted into a user is taken at each of the receiving antennas during a period of time. The measurements of the signal are processed using a DFT. In an embodiment, the measurements are processed using an FFT. The processed signals are then used to generate a graphical depiction of the signals measurements, such as the graphical depictions shown in FIGS. 4 and 5.

FIG. 4 is a graph illustrating the processed signals received from a sensor system positioned proximate to the abductor pollicis longus tendon in the arm. The sensor system is able to take measurements of the received signals and process the received signals to provide the fluctuating line shown in the figures. Changes in the processed signal are correlated with activity being performed by a user. The change in signal reflected by the formation of a peak in the graph shown in FIG. 4 occurs when a person pinches by placing their forefinger to their thumb. When contact is made the peak in the graph occurs. FIG. 5 is another view of a mechanomyogram taken when a person is pinching. When the contact is released, the signal changes, which is illustrated by the dip in the signal.

Mechanical movements of the muscles can be sensed and measured using the sensor system described above. Depending on the placement and orientation of the sensor system and its components various activities can be correlated with different muscle movements and activities detected by the sensors. Placement of the sensing system with respect to the wrist area has been able to enhance the ability of the sensing system to be able to distinguish types of events that may be difficult to detect otherwise. By placing the sensing system in a location where data with respect to the movement of the wrist and movement of the fingers reflected within the area of the wrist are able to be determined such previously elusive events can be detected. By correlating certain events with the determined activity within the wrist area, events such as touch, pinch and the touching of objects can be discerned. Furthermore, via the usage of machine learning the ability to determine events can be enhanced as more correlating events are ascribed to the use of the sensing system.

Figure 6:
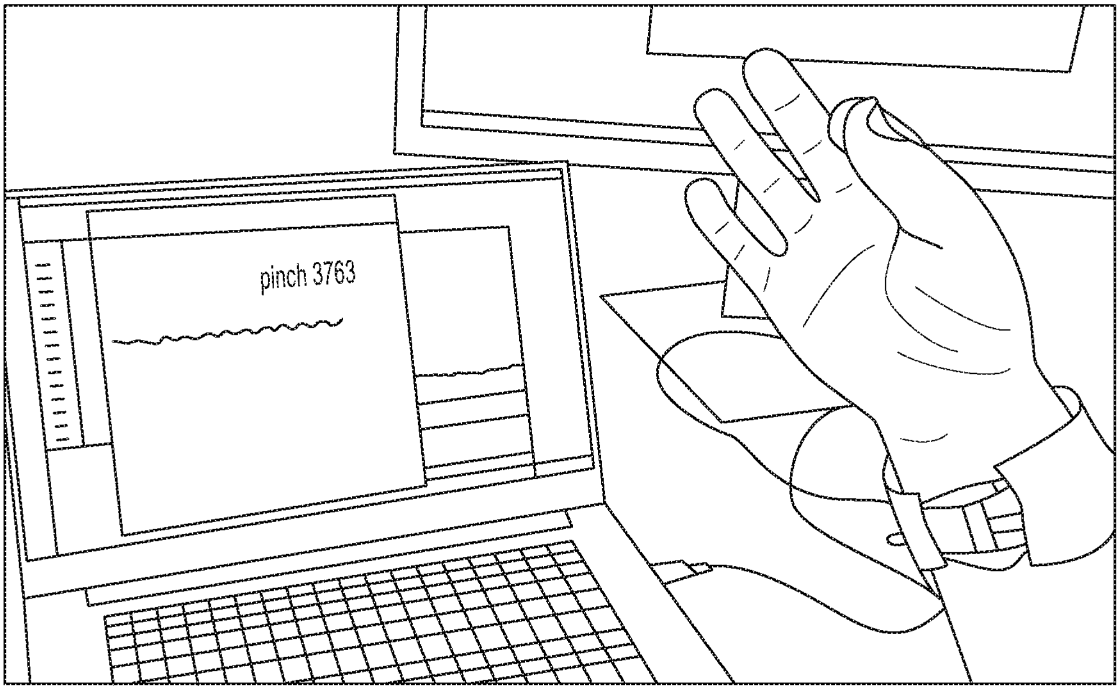
FIG. 6 is an example of a sensing system and output display showing a pinch being detected.
Figure 7:
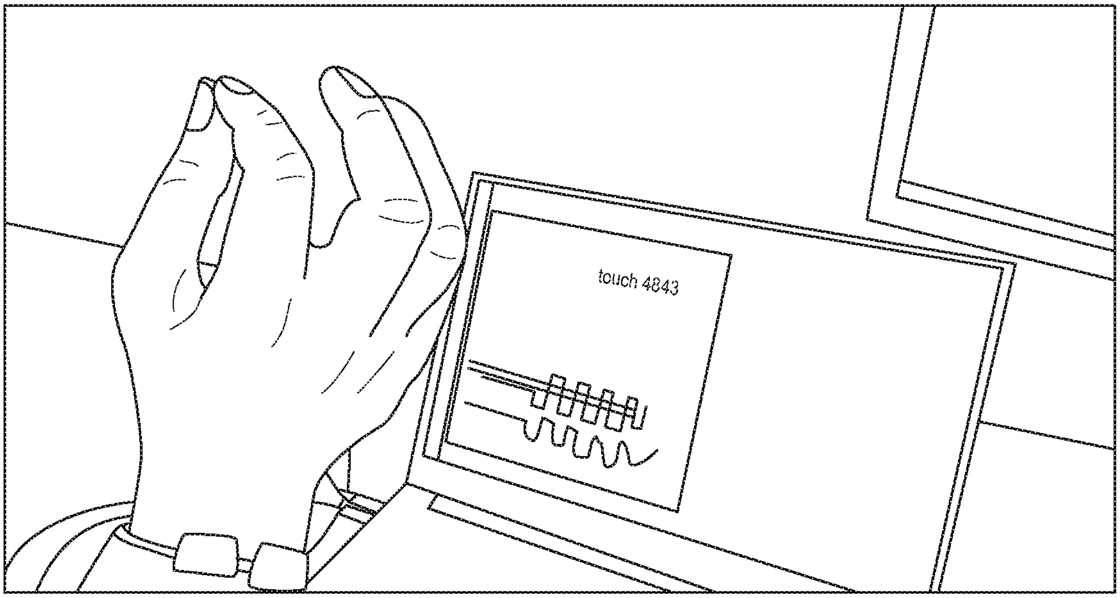
FIG. 7 is an example of a sensing system and output display showing a touch of two fingertips being detected.

For example, in the signals received, processed and graphically depicted in FIGS. 6-9, a sensor placed at a certain location on the arm (e.g. over the abductor pollicis longus tendon) is able to detect and determine movement that is correlated to the pinch and unpinching activity of a person's hand. FIG. 6 shows a pinch being determined by the sensing system. The transmitting and receiving antennas are placed proximate to the wrist area. The movement and position of physical structure of bones, tendons, veins, arteries, etc. within the wrist area impact the measurement of signals that are received. The measured signals are used in order to determine the motion of the fingers and determine other hand related behaviors. FIG. 6 shows a pinch between the index finger and the thumb being detected and determined by the sensing system. FIG. 7 shows the sensing system being able to determine when touch (not a full force pinch) between the index finger and the thumb occurs.

Thus different gradients of the movement and activity can be determined by the sensing system. The movement of the surface of the skin with respect to the receiving antennas is able to be discerned. Due to the different movements of the interior structure of the wrist area and its impact on the movement of the skin, different types of behaviors and activities are able to be determined. Placement of the sensing system can determine what types of activities can be determined. For example, the placement of the transmitting antennas and the receiving antennas on the top portion of the wrist area (i.e. the area shown in the figures where the sensing system is placed) has been determined to be effective for detecting the internal movements within the wrist area that can be correlated to pinch and fingertips touching. Placement of the sensing system in certain locations on a user enables different types of activity to be determined. Additionally, characteristics of a load that is placed on any given muscle can be determined from the processed signals.

Figure 8:
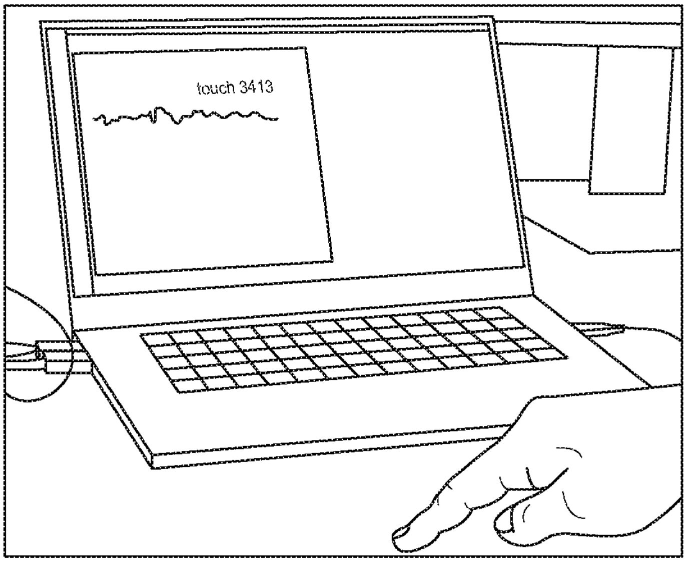
FIG. 8 is an example of a sensing system and output display showing a touch of a table being detected.
Figure 9:
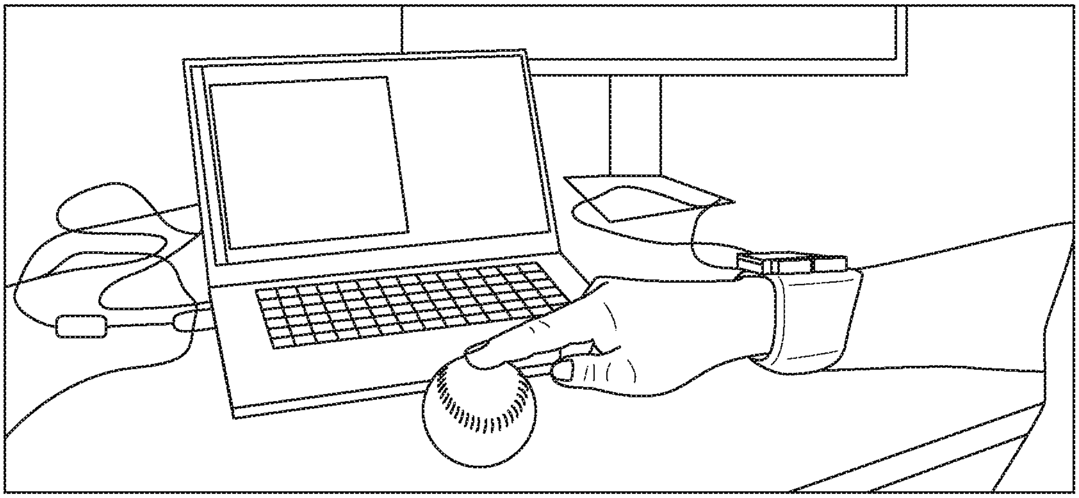
FIG. 9 is an example of a sensing system and output display showing a touch of a ball being detected.

FIG. 8 shows a touch of table being determined by the sensing system. Depending on the measured signals the type of touch can be qualified, so that the sensing system is able to determine when an inanimate object is pressed. FIG. 9 shows a touch of a baseball being determined by the sensing system. In both situations the touch event is being determined by contact of the finger with the surface of an object and resultant impact that the touch event has on the underlying physical structure within the wrist area. This activity is able to be determined and distinguished from the determination of a pinch.

The location and placement of the sensor system can be correlated with the activity or movement that is the focus of activity. In an embodiment, placement of the sensor system is correlated with making a fist. In an embodiment, placement of the sensor system is correlated with making a hand gesture. In an embodiment, placement of the sensor system is correlated with facial expressions. In an embodiment, placement of the sensor system is correlated with foot movement. In an embodiment, placement of the sensor system is correlated with leg motion. In an embodiment, placement of the sensor system is correlated with hip motion. In an embodiment, placement of the sensor system is correlated with vocal activity. In an embodiment, placement of the sensor system is correlated with arm motion. In an embodiment, placement of the sensor system is correlated with head motion. In an embodiment, placement of the sensor system is correlated with chest activity. In an embodiment, placement of the sensor system is correlated with back activity. In an embodiment, more than one of these placements is used to determine various compound or complicated activities. In an embodiment, a sensor system is placed to determine passive activity of muscles. In an embodiment, a sensor system is placed to determine oscillations of muscles. In an embodiment, a sensor system is placed to determine resonant frequencies of muscles.

Figure 10:
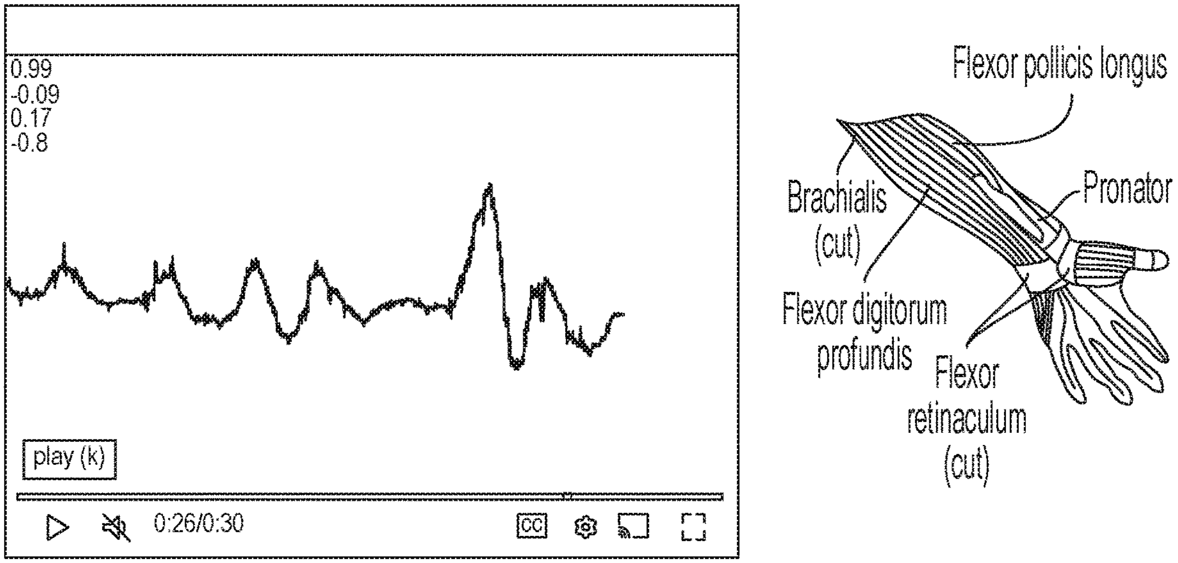
FIG. 10 is a mechanomyogram showing oscillations of a muscle.
Figure 11:
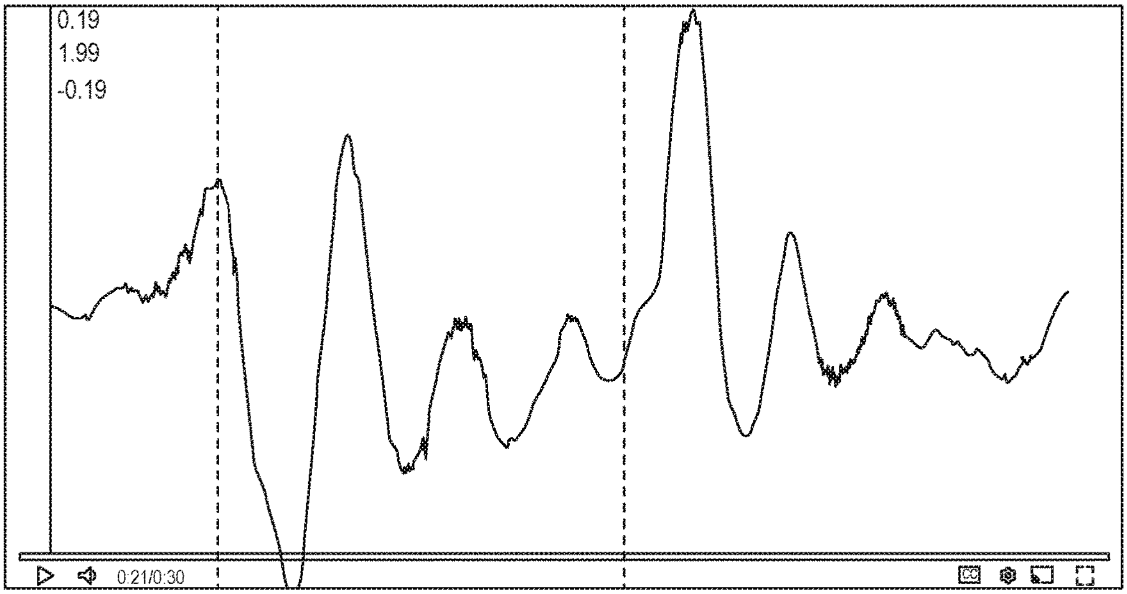
FIG. 11 is another mechanomyogram showing oscillation of a muscle.
Figure 12:
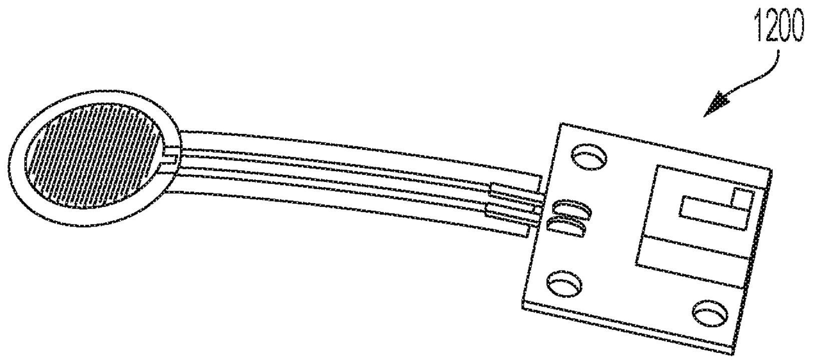
FIG. 12 shows an example of a piezoelectric sensor able to be implemented into the sensor system.

FIGS. 10 and 11 show mechanomyograms generated by an embodiment of a sensor system that implements piezoelectric sensors within the sensor system, such as the piezoelectric sensor 1200 shown in FIG. 12. The mechanomyograms reflect movement and oscillation of muscles in the body. The piezoelectric sensor 1200 generates a signal based on movements and vibrations. This generated signal is then received at receiving antennas and are processed to determine information regarding muscle activity. This measured activity can be used for the same purposes for which traditional mechanomyography is used. In embodiment, the piezoelectric sensors are used in addition to the transmitting antenna that infuses signal. In an embodiment, both the piezoelectric sensors and the transmitting antenna are used simultaneously. In an embodiment, the piezoelectric sensors and the transmitting antenna are used in alternating fashion. In an embodiment, the piezoelectric sensors and the transmitting antenna provide measurements that are compiled together to provide additional information regarding muscle activity. In embodiment, the piezoelectric sensors and the transmitting antenna provide measurements that are cross-checked to provide verifying information regarding muscle activity.

Figure 13:
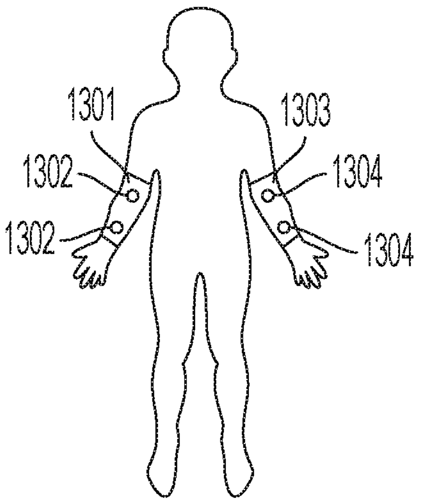
FIG. 13 is a diagram of an individual having transmitting and receiving antennas placed on the body.

FIG. 13 is a simple diagram illustrating an embodiment of transmitting antennas 1302 and receiving antennas 1304 that can be used in order to determine information regarding movement and activity of the user. The transmitting antennas 1302 and the receiving antennas 1304 may also be referred to as electrodes or conductors. The transmitting antennas 1302 are adapted to transmit signals that are then received by the receiving antennas 1304. The transmitting antennas 1302 are located on a substrate 1301 that separates the transmitting antennas 1302 from the surface of the skin. The receiving antennas 1304 are located on a substrate 1303 that separates the receiving antennas 1304 from the surface of the skin. The substrates 1301 and the substrate 1303 may be formed as a type of sleeve, or other wearable, that can easily conform to a user's arm or otherwise be worn by the user. While the transmitting antennas 1302 and the receiving antennas 1304 are formed as two different sleeves, in an embodiment, the transmitting antennas and receiving antennas are located on the same sleeve. In an embodiment, the sleeve having the receiving antennas is the sleeve that may be placed proximate to the area that has muscle activity that is to be detected while the transmitting antennas may be located elsewhere on the user or in the environment. In an embodiment, both sleeves may be part of the same shirt or jacket. In an embodiment, each sleeve is a separate garment that can be placed on an arm.

It should be understood that the transmitting antennas 1302 and the receiving antennas 1304 may function in opposite roles, that is to say the transmitting antennas 1302 can function as the receiving antennas 1304 and vice versa. Furthermore, their respective roles can vary as needed. In an embodiment, a single frequency signal is transmitted by a transmitting antenna 1302. In an embodiment, a plurality of orthogonal signals that are orthogonal with respect to each other are transmitted by the transmitting antennas 1302. In an embodiment, a plurality of frequency orthogonal signals that are orthogonal with respect to each other are transmitted by the transmitting antennas 1302. Those signals that are received by the receiving antennas 1304 are measured and processed. This measurement permits capacitive determination of muscle activity. The processed signals are correlated with muscle activity. The processed signals can be used in order to ascertain information related to muscles such as muscle fatigue, strength and balance. Additionally, the determination and production of mechnomyograms can be correlated with muscle activity and movements related to various activities expressed by the muscles, such as finger movements (e.g. pinch, grasp, etc.), opposition (touching of thumb to fingers), arm movements, and movements of other body parts.

FIG. 13 shows the antennas placed on each arm of a person. However, this arrangement is simply shown in this manner by way of example. The arrangement of the transmitting antennas 1302 and the receiving antennas 1304 are placed on the body at locations where meaningful information about the muscle activity can be obtained. In an embodiment, the transmitting antennas and the receiving antennas are placed on portions of each arm. In an embodiment, the transmitting antennas and the receiving antennas are placed on portions of the same arm. In an embodiment, the transmitting antennas and the receiving antennas are placed on the upper portion of an arm. In an embodiment, the transmitting antennas and the receiving antennas are placed on the forearm of a person. In an embodiment, the transmitting antennas and the receiving antennas are placed on the hand of a person. In an embodiment, the transmitting antennas and the receiving antennas are placed on the wrist of a person. In an embodiment, the transmitting antennas and the receiving antennas are placed on each leg of a person. In an embodiment, the transmitting antennas and the receiving antennas are placed on the thigh of a person. In an embodiment, the transmitting antennas and the receiving antennas are placed on the lower leg of a person. In an embodiment, the transmitting antennas and the receiving antennas are placed on the ankle of a person. In an embodiment, the transmitting antennas and the receiving antennas are placed on the foot of a person. In an embodiment, the transmitting antennas and the receiving antennas are placed on the chest of a person. In an embodiment, the transmitting antennas and the receiving antennas are placed on the torso of a person. In an embodiment, the transmitting antennas and the receiving antennas are placed in the neck region of a person. In an embodiment, the transmitting antennas and the receiving antennas are placed on the head of a person. In an embodiment, the transmitting antennas and the receiving antennas are placed in any combination of the above referenced positions.

In an embodiment, the transmitting antennas and the receiving antennas may be placed in such a way that they are in direct contact with an individual's skin. In an embodiment, the transmitting antennas and the receiving antennas may be placed in such a way that they are located proximate to but are not in direct contact with an individual.

Figure 14:
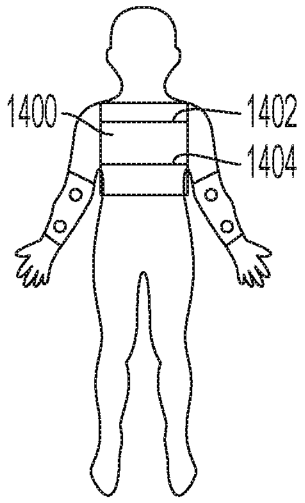
FIG. 14 is a diagram of an individual having transmitting and receiving antennas worn on a garment.

Referring now to FIG. 14, FIG. 14 shows a simple diagram of a person wearing a garment 1400 that has embedded therein transmitting antennas 1402 and receiving antennas 1404. The transmitting antennas 1402 and the receiving antennas 1404 may also be referred to as electrodes or conductors. The transmitting antennas 1402 are adapted to transmit signals that are then able to be received by the receiving antennas 1404. It should be understood that the transmitting antennas 1402 and the receiving antennas 1404 may function in different roles, that is the transmitting antenna 1402 can function as the receiving antenna 1404 and vice versa. In an embodiment, a plurality of orthogonal signals that are orthogonal with respect to each other are transmitted by the transmitting antennas 1402. In an embodiment, a single frequency signal is transmitted by a transmitting antenna 1402. In an embodiment, a plurality of frequency orthogonal signals that are orthogonal with respect to each other are transmitted by the transmitting antennas 1402. Those signals that are received by the receiving antennas 1404 are measured and processed. The processed signals are correlated with muscle activity. This is then used in order to ascertain information related to muscles such as muscle fatigue, strength and balance.

In an embodiment, the garment 1400 is a textile formed with transmitting antennas 1402 and receiving antennas 1404. In an embodiment, the garment 1400 is formed from leather. In an embodiment, the garment 1400 is formed from lycra. In an embodiment, the garment 1400 is formed from neoprene material. In an embodiment, the garment 1400 is made from an organic material with antennas threaded throughout the garment 1400. In an embodiment, the garment 1400 is made from a synthetic material with antennas threaded throughout the garment 1400. In an embodiment, the garment 1400 is made from a combination of synthetic and organic materials.

In FIG. 14, the garment 1400 is shown worn in the chest area and is able to determine muscle activity within that area. In an embodiment, the garment is formed as a shirt. Transmitting antennas and receiving antennas in a garment formed as a shirt are able to determine activity in the chest area and in areas proximate to the arms. The arrangement of the transmitting antennas and the receiving antennas are placed in the garment proximate to areas on the body at locations where meaningful information about the muscle activity can be obtained. In an embodiment, the transmitting antennas and the receiving antennas are placed in the garment proximate portions of each arm. In an embodiment, the transmitting antennas and the receiving antennas in the garment are placed proximate to locations on the same arm. In an embodiment, the transmitting antennas and the receiving antennas are placed in the garment proximate to an upper portion of an arm. In an embodiment, the transmitting antennas and the receiving antennas are in a garment proximate to the forearm. In an embodiment, the garment is formed as a glove. In an embodiment, the garment is formed as a bracelet. In an embodiment, the garment is formed as pants. In an embodiment, the transmitting antennas and the receiving antennas are proximate to the thigh of a person located within pants. In an embodiment, the transmitting antennas and the receiving antennas are proximate to the lower leg of a person. In an embodiment, the transmitting antennas and the receiving antennas are placed proximate to the ankle of a person located within pants, socks or an ankle bracelet. In an embodiment, the transmitting antennas and the receiving antennas are placed on the foot of a person located within socks or formed as shoes. In an embodiment, the transmitting antennas and the receiving antennas are placed on the chest of a person formed as a shirt. In an embodiment, the garment is formed as a shirt located proximate to a person's torso and able to obtain information regarding a person's torso. In an embodiment, the transmitting antennas and the receiving antennas are formed as a necklace or formed as a scarf. In an embodiment, the transmitting antennas and the receiving antennas are formed as a hat. In an embodiment, the transmitting antennas and the receiving antennas are placed in multiple garments worn by an individual. It should be understood that while reference is made to more than one transmitting antenna and more than one receiving antennas the garments can be formed using only one transmitting antenna and multiple receiving antennas or one receiving antenna and multiple transmitting antennas.

Figure 15:
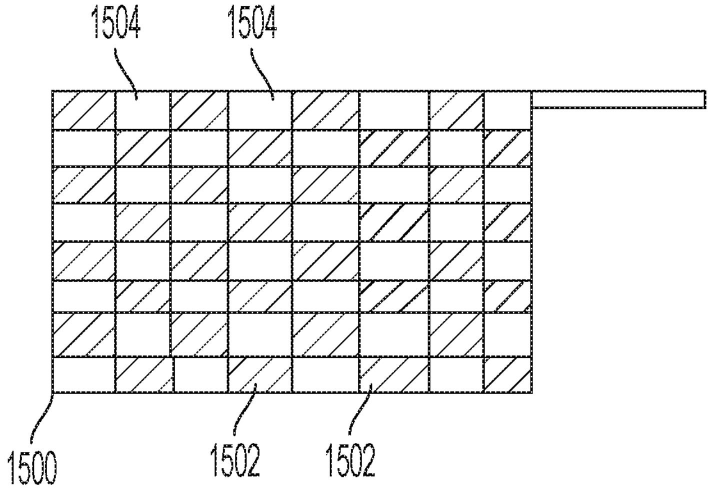
FIG. 15 is a diagram of a sensor array.
Figure 16:
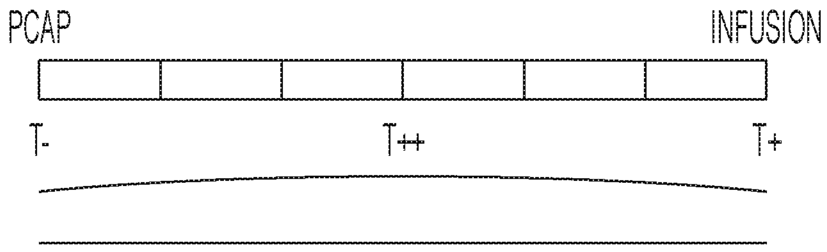
FIG. 16 is a diagram showing measurement of signals of the sensor array shown in FIG. 15.

Turning to FIGS. 15 and 16, shown is an embodiment of a sensing system that implements both PCAP (Projected Capacitance) and infusion based sensing. In this embodiment, complementary measurements of signals can provide a varied and robust determination of muscle movement and its correlating user activity. In FIG. 15, shown is a sensing system 1500 having a checkerboard matrix pattern of transmitting antennas 1502 and receiving antennas 1504. It should be understood that the functions of the transmitting antennas 1502 and receiving antennas 1504 may be alternated or changed depending on the sensing modality that is being pursued. In FIG. 15, each of the transmitting antennas 1502 is adapted to transmit a signal that is orthogonal to each other signal transmitted. In an embodiment, each of the orthogonal signals are frequency orthogonal with respect to each other of the signals that are transmitted.

Referring to FIG. 16, shown is a diagram illustrating the measurement of signals processed by the receiving antenna depending on the type of measurement being performed and the proximity of the receiving antenna to the transmitting antenna. The sensing mode being used will determine properties of the signal being measured. For the purposes of illustration, the signal received can either be measured as T+ or its inverse T− depending on the sensing mode being implemented by the sensing system 1500. During PCAP based sensing, the approach of the capacitive object, i.e. the surface of the skin, to the sensor system impacts the amount of signal that is measured at a receiving antenna as signal is drawn into the capacitive object. The resultant measurement is then T−. During infusion sensing, as the surface of the skin carrying the infused signal approaches a receiving antenna the signal from the surface of the skin is measured, the resultant measurement being T+. By combining the two different sensing modalities additional information regarding the movement of the surface of the skin with respect to each of the receiving antennas can be determined based on comparing the amount of signal measured during PCAP sensing with the amount of signal measured during infusion sensing.

It should be understood that while the above systems are described in terms of muscle activity of a person, other animals and creatures that have muscles can also benefit from the application of the electrodes and/or the antennas. It should also be understood that muscle activity includes muscle activity that is not the result of voluntary movement and includes involuntary movements, such as muscle twitching, oscillation and/or vibrations.

Various applications of the muscle activity determination can be used in order to provide therapeutic benefits. Through the determination of muscle activity physical therapy can be prescribed and adhered to through the monitoring of activity that a person performs while utilizing a sensing system that implements the measuring techniques discussed above. Various muscle groupings can be focused on and exercised in order to improve the muscular ability of a person. For example, with respect to the determination of activity related to the finger movement, such as the pinch discussed above, a person can actively monitor and exercise those particular muscles and be able to obtain diagnostic information related to the strength of movement and the efficacy of the activity.

An aspect of the disclosure is a sensing system for determining muscle activity. The sensing system comprising: a transmitting antenna adapted to transmit at least one signal into a user of the sensing system; a plurality of receiving antennas, each one of the plurality of receiving antennas adapted to receive the at least one signal transmitted into the user; and a processor adapted to process measurements for each one of the plurality of receiving antennas of the at least one signal transmitted into the user received by each one of the plurality of receiving antennas and determine muscle activity based on the processed measurements.

An aspect of the disclosure is a sensing system for determining muscle activity. The sensing system comprising: a transmitting antenna adapted to transmit signals into a user of the sensing system; a plurality of receiving antennas, each one of the plurality of receiving antennas adapted to receive signal transmitted into the user; and a processor adapted to process a measurement of signals received for each one of the plurality of receiving antennas and use processed measurements of signal to form a mechanomyogram used to determine muscle activity of the user.

Another aspect of the disclosure is a method for determining muscle activity. The method comprising; simultaneously transmitting a plurality of signals into a body of a user, wherein each of the plurality of signals transmitted are frequency orthogonal with respect to each other of the simultaneously transmitted plurality of signals transmitted; and receiving at least one of the transmitted plurality of signals on at least one of a plurality of receiving antennas; and processing received signals to produce a mechanomyogram.

While the invention has been particularly shown and described with reference to a preferred embodiment thereof, it will be understood by those skilled in the art that various changes in form and details may be made therein without departing from the spirit and scope of the invention.

The invention claimed is:

1. A sensing system for determining muscle activity, comprising:

a plurality of transmitting antennas and receiving antennas located on a band, the transmitting antennas and receiving antennas forming a matrix;

a mixed signal integrated circuit adapted to generate a plurality of frequency orthogonal signals to provide to the plurality of transmitting antennas;

the plurality of transmitting antennas adapted to infuse the plurality of frequency orthogonal signals into a user of the sensing system and to transmit the plurality of frequency orthogonal signals for a capacitive sensing mode;

each one of the plurality of receiving antennas adapted to receive the plurality of frequency orthogonal signals that have been infused into the user and the plurality of frequency orthogonal signals transmitted for the capacitive sensing mode, wherein the received plurality of frequency orthogonal signals that have been infused into the user are used for an infusion sensing mode and the plurality of frequency orthogonal signals transmitted for the capacitive sensing mode are used for the capacitive sensing mode; and a processor adapted to determine, based on comparing the received infused plurality of frequency orthogonal signals and the transmitted plurality of frequency orthogonal signals used in the capacitive sensing mode, muscle activity.

2. The sensing system of claim 1, wherein the muscle activity determined is opposition of a user's fingers.

3. The sensing system of claim 1, wherein the muscle activity determined is touching of an object.

4. The sensing system of claim 1, wherein the muscle activity determined is whether or not fingers have touched or pinched.

5. The sensing system of claim 1, wherein the muscle activity is used to create a mechanomyogram.

6. The sensing system of claim 5, wherein the mechanomyogram is used to determine oscillation and vibration of muscles.

7. The system of claim 1, wherein the plurality of transmitting antennas and the plurality of receiving antennas are alternated.

8. A sensing system for determining muscle activity, comprising:

a plurality of transmitting antennas and receiving antennas forming a matrix located within a vehicle;

a mixed signal integrated circuit adapted to generate a plurality of frequency orthogonal signals to provide to the plurality of transmitting antennas;

the plurality of transmitting antennas adapted to infuse the plurality of frequency orthogonal signals into a user of the sensing system and to transmit the plurality of frequency orthogonal signals for a capacitive sensing mode;

each one of the plurality of receiving antennas adapted to receive the plurality of frequency orthogonal signals that have been infused into the user and the plurality of frequency orthogonal signals transmitted for the capacitive sensing mode, wherein the received plurality of frequency orthogonal signals that have been infused into the user are used for an infusion sensing mode and the plurality of frequency orthogonal signals transmitted for the capacitive sensing mode are used for the capacitive sensing mode; and a processor adapted to determine, based on comparing the received infused plurality of frequency orthogonal signals and the transmitted plurality of frequency orthogonal signals used in the capacitive sensing mode, muscle activity.

9. The sensing system of claim 8, wherein the determined muscle activity comprises a pinching of a thumb and one other finger of a hand.

10. The sensing system of claim 8, wherein the determined muscle activity is used to determine a mechanomyogram that is used to determine oscillation and vibration of muscles.

11. The system of claim 8, wherein the plurality of transmitting antennas and the plurality of receiving antennas are alternated.

* * * * *